United States Patent [19] [11] Patent Number: 4,920,451
Sakai et al. [45] Date of Patent: Apr. 24, 1990

[54] MOISTURE-SENSITIVE ELEMENT

[75] Inventors: Yoshiro Sakai; Yoshihiko Sadaoka, both of Ehime; Takaai Kuroiwa, Kanagawa; Tooru Abe, Kanagawa; Tetsuya Miyagishi, Kanagawa, all of Japan

[73] Assignee: Yamatake-Honeywell Co., Ltd., Tokyo, Japan

[21] Appl. No.: 353,903

[22] Filed: May 18, 1989

[30] Foreign Application Priority Data

May 23, 1988 [JP] Japan .............................. 63-66813[U]
Jun. 14, 1988 [JP] Japan ................................ 63-144665
Aug. 17, 1988 [JP] Japan ................................ 63-203154

[51] Int. Cl.$^5$ ........................ H01G 5/20; G01N 25/64
[52] U.S. Cl. ..................................... 361/286; 73/336.5

[58] Field of Search ....................... 361/286; 73/336.5; 324/61 P

[56] References Cited

U.S. PATENT DOCUMENTS 3,983,527  9/1976  Ohsato et al. .................. 73/336.5 X
4,164,868  8/1979  Suntola ............................ 73/336.5
4,442,422  4/1984  Murata et al. ................. 73/336.5 X
4,558,393  12/1985  Tanaka et al. ..................... 361/286

Primary Examiner—Donald A. Griffin
Attorney, Agent, or Firm—Blakely, Sokoloff, Taylor & Zafman

[57] ABSTRACT

A moisture-sensitive element includes a moisture-sensitive film consisting of a polymer prepared by polymerizing a methacrylate monomer not having a hydroxyl group. A humidity detector using the moisture-sensitive element is also disclosed.

8 Claims, 6 Drawing Sheets

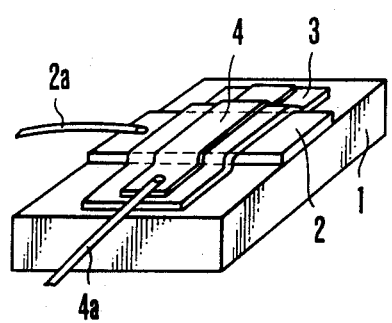
F I G. 1
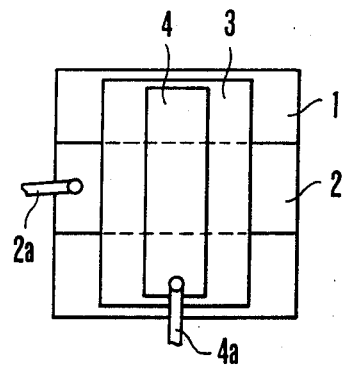
F I G. 2
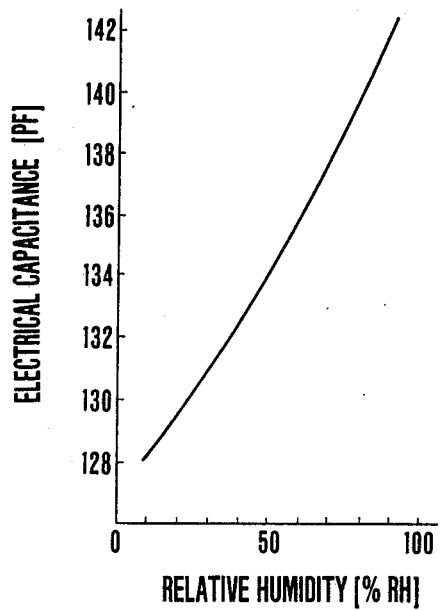
F I G. 3

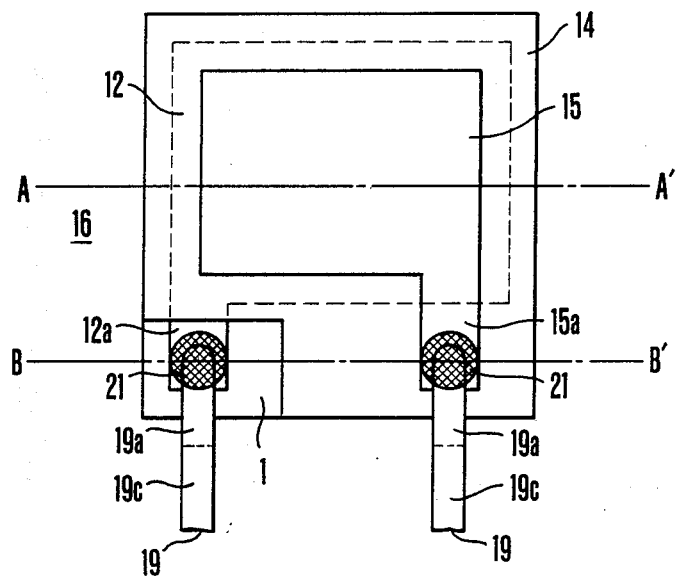
F I G. 6 (A)
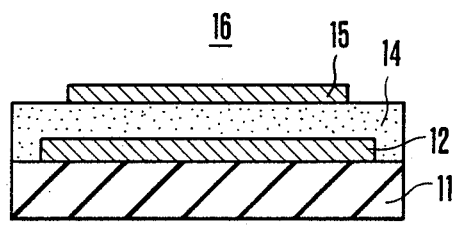
F I G. 6 (B)
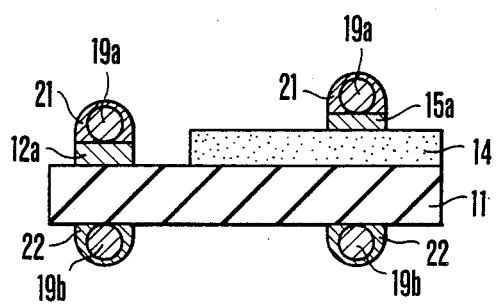
F I G. 6 (C)

MOISTURE-SENSITIVE ELEMENT

BACKGROUND OF THE INVENTION

1. Field of the Invention

The present invention relates to a moisture-sensitive element and a humidity detector using the same.

2. Prior Art

A conventional moisture-sensitive element uses an organic polymer such as celluloseacetatebutyrate, celluloseacetatepropyonate, polyimide, or polyimideamide as a moisture-sensitive material and utilizes an electrical capacitance change in moisture-sensitive film formed by this moisture-sensitive material to detect humidity (Japanese Patent Laid-Open No. 62-88951).

A moisture-sensitive element having the above arrangement, however, has a high hydrophilic nature and a large water sorption amount (water absorption ratio). Therefore, a large amount of water strongly bonded to the polymer remains. For this reason, when the element is used in a high-temperature, high-humidity atmosphere, e.g., at a temperature of 40° C. and a humidity of 90% for a long period of time, its output value drifts. In addition, a moisture-sensitivity characteristic difference (hysteresis) between moisture absorption and desorption processes is decreased at a low-temperature side and increased at a high-temperature side, thereby delaying sensor response. Furthermore, an output value of the element drifts due to moisture condensation or water dipping.

In a conventional moisture-sensitive element, a moisture-sensitive film is sandwiched between lower and upper electrodes, and an electrical signal is extracted from external lead wires directly connected to terminals of the electrodes.

In the moisture-sensitive element having the above arrangement, however, the external lead wires are electrically and mechanically connected to the electrode terminals by solder. Therefore, a mechanical stress or vibration is externally applied to the lead wires, or degradation occurs due to a repetitive moisture absorption/dry cycle or a temperature cycle, thereby causing a contact failure. A moisture-sensitive element using conductive rubber in place of an external lead wire to be connected to electrode terminals is available. In this moisture-sensitive element, however, fatigue or permanent deformation of the conductive rubber or a vibration leads to a contact failure. A moisture-sensitive element using a conductive adhesive in place of the solder for connecting the electrode terminals and the external lead wires is also available. In this moisture-sensitive element, however, when a mechanical stress or vibration is externally applied to the external lead wires, the force directly acts on the conductive adhesive portion having low strength. Therefore, film peeling or a contact failure tends to occur upon handling or actual use, resulting in poor handling properties and reliability.

Such a moisture-sensitive element is incorporated in a humidity detector as disclosed in, e.g., Japanese Utility Model Laid-Open No. 61-69153.

In such a humidity detector, however, although a porous filter consisting of a repellent material is mounted in an opening portion of a main body case to prevent attachment of water, dust, tobacco smoke, salts or the like to the surface of the moisture-sensitive element, a sealing property between the filter and the main body case is unsatisfactory. Therefore, when the detector is dipped and used in water, water reaches the moisture-sensitive element to cause inconvenience. For this reason, after the humidity detector is used for a long time period, it cannot be washed with water to remove foreign matters adhered on the porous filter.

SUMMARY OF THE INVENTION

It is a principal object of the present invention to provide a moisture-sensitive element having a small hysteresis and a high response speed throughout an operation range from low to high temperature and humidity.

It is another object of the present invention to provide a moisture-sensitive element which can stably output even after it is used under conditions of high humidity, high temperature and humidity, a humidity cycle, moisture condensation, or water dipping for a long period of time.

It is still another object of the present invention to provide a moisture-sensitive element having good heat, solvent, and environmental resistances.

It is still another object of the present invention to provide a moisture-sensitive element in which electrode terminals are strongly connected to external lead wires, thereby realizing highly reliable connections.

It is still another object of the present invention to provide a moisture-sensitive element which can be manufactured by a smaller number of manufacturing steps at low cost.

It is still another object of the present invention to provide a humidity detector which can improve a sealing property between a main body case for housing a moisture-sensitive element and a filter, thereby improving reliability and a service life of the element.

According to an aspect of the present invention, there is provided a moisture-sensitive element comprising a moisture-sensitive film consisting of a polymer prepared by polymerizing a methacrylate monomer not having a hydroxyl group.

According to another aspect of the present invention, there is provided a moisture-sensitive element comprising a moisture-sensitive film consisting of a polymer prepared by copolymerizing a methacrylate monomer not having a hydroxyl group and a crosslinking agent having a plurality of vinyl groups.

According to still another aspect of the present invention, there is provided a humidity detector, wherein at least one opening portion is formed in a case housing a moisture-sensitive element, and a hydrophobic filter is arranged on the opening portion via a bonding agent, the moisture-sensitive element comprising a moisture-sensitive film consisting of a polymer prepared by polymerizing a methacrylate monomer not having a hydroxyl group.

According to still another aspect of the present invention, there is provided a humidity detector, wherein at least one opening portion is formed in a case housing a moisture-sensitive element, and a hydrophobic filter is arranged on the opening portion via a bonding agent, the moisture-sensitive element comprising a moisture-sensitive film consisting of a polymer prepared by copolymerizing a methacrylate monomer not having a hydroxyl group and a crosslinking agent having a plurality of vinyl groups.

BRIEF DESCRIPTION OF THE DRAWINGS

FIG. 1 is a perspective view showing an embodiment of a moisture-sensitive element according to the present invention;

FIG. 2 is a plan view showing the moisture-sensitive element;

FIG. 3 is a graph showing relative humidity-electrical capacitance characteristics of the moisture-sensitive element;

FIGS. 6A, 6B, and 6C are a plan view showing a main part of the moisture-sensitive element according to another embodiment of the present invention, a sectional view taken along a line A—A' in FIG. 6A, and a sectional view taken along a line B—B' in FIG. 6A, respectively;

DETAILED DESCRIPTION OF THE PREFERRED EMBODIMENTS

Figure 4:
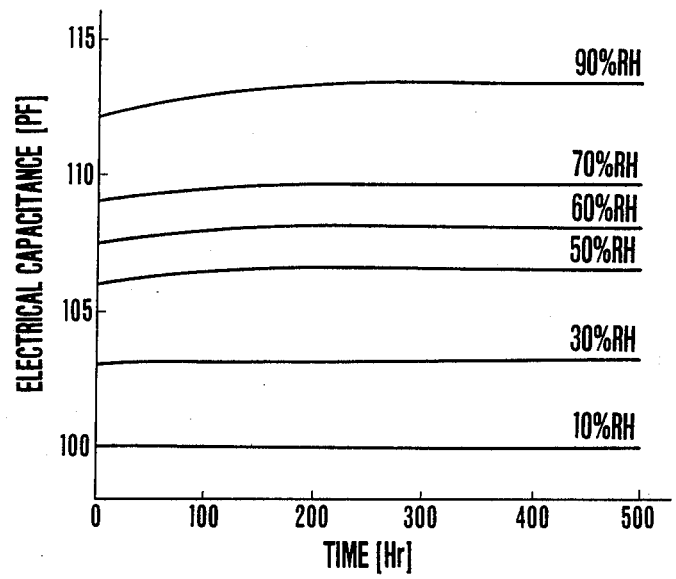
FIG. 4 is a graph showing moisture-sensitivity characteristics of the moisture-sensitive element according to the present invention.

Embodiments of the present invention will be described in detail below with reference to the accompanying drawings.

FIG. 1 shows an embodiment of a moisture-sensitive element according to the present invention, and FIG. 2 shows a plan view thereof. Referring to FIGS. 1 and 2, reference numeral 1 denotes an insulating substrate comprising an alumina substrate, a glass substrate, a thermal oxide silicon substrate or the like; 2, a lower electrode formed on the upper surface of the insulating substrate 1 and consisting of, e.g., platinum; 3, a moisture-sensitive film stacked on and across the lower electrode 2; and 4, an upper electrode formed on the moisture-sensitive film 3 and consisting of, e.g., gold. That is, the moisture-sensitive film 3 is sandwiched between the lower and upper electrodes 2 and 4. In addition, in order to detect an electrical capacitance change in the moisture-sensitive film 3 with respect to a relative humidity, strip lead wires 2a and 4a are connected to the lower and upper electrodes 2 and 4, respectively.

In the moisture-sensitive element having the above arrangement, the moisture-sensitive film 3 consists of a moisture-sensitive material prepared by polymerizing methyl methacrylate or a moisture-sensitive material prepared by copolymerizing methyl methacrylate and divinylbenzene.

A method of manufacturing the moisture-sensitive element will be described in detail below.

A methyl methacrylate monomer (MMA) purified by reduced-pressure distillation is prepolymerized in the presence of a catalyst to prepare a solution having proper viscosity. This solution is coated by a spin coating method on the lower electrode 2 formed on the insulating substrate 1, and is heated at 90° C. to 200° C. to complete polymerization, thereby forming the moisture-sensitive film 3 having a thickness of 0.5 to 10 μm. At this time, a rotational speed of a spinner is 1,000 to 5,000 rpm. Gold is adhered by a evaporating or sputtering method on the insulating substrate 1 on which the moisture-sensitive film 3 is stacked. Thus, the upper electrode 4 having a thickness of 50 to 500 Å is formed. Note that the lower electrode 2 on the insulating substrate 1 is formed to be a thin film having a thickness of 1,000 to 10,000 Å by evaporating or sputtering platinum. In this case, the moisture-sensitive film 3 consists of a methyl polymethacrylate (PMMA) homopolymer prepared from a methyl methacrylate monomer (MMA) as a starting material without crosslinking.

With the above arrangement, since the moisture-sensitive film 3 consists of a methyl polymethacrylate (PMMA) homopolymer, a water sorption amount and hysteresis are reduced.

When the relative humidity-electrical capacitance characteristics of the moisture-sensitive element having the above arrangement were measured, data as shown in FIG. 3 was obtained. Note that the measurement was performed at a temperature of 25° C. and a frequency of 100 kHz by using an LCZ meter. As is apparent from FIG. 3, the hysteresis was about 1% RH or less, typically 0.3% RH, i.e., was very good.

Another embodiment of the moisture-sensitive element according to the present invention will be described below with reference to FIGS. 1 and 2.

A methyl methacrylate monome (MMA) is prepolymerized in the presence of a catalyst, and divinylbenzene (about 30 wt % or less with respect to the MMA) is added as a hydrophobic crosslinking agent, thereby preparing a solution. This solution is coated by a spin coating method on a lower electrode 2 formed on an insulating substrate 1, and is heated and copolymerized at about 90° C. to 200° C. to form a 0.5- to 10-μm thick moisture-sensitive film 3, thereby completing a moisture-sensitive element. In this case, the moisture-sensitive film 3 consists of a methyl polymethacrylate-divinylbenzene copolymer prepared from a methyl methacrylate monomer (MMA) and divinylbenzene as starting materials, and is crosslinked.

Note that in the above embodiment, a catalyst can be additionally used upon addition of divinylbenzene.

With the above arrangement, since the moisture-sensitive film 3 consists of a copolymer containing a hydrophobic crosslinking agent, a water absorption ratio is reduced lower than that of a methyl polymethacrylate (PMMA) homopolymer. Therefore, a water sorption amount can be finely controlled to realize a polymer having an optimal water sorption amount for achieving target characteristics. In addition, the film characteristics can be further improved. That is, in a solvent dipping test in which the moisture-sensitive element having the above arrangement was dipped in a solution of, e.g., ethyl acetate, acetone, toluene, dioxane, ethanol, carbon tetrachloride, benzene, ethylene dichloride, n-hexane, or cycrohexane, the moisture-sensitive element was not dissolved at all, i.e., its solvent resistance was improved.

Figure 5:
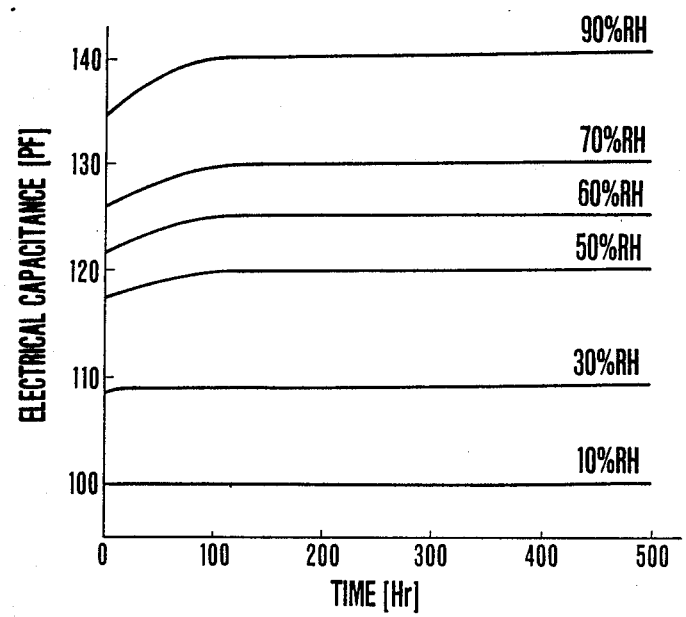
FIG. 5 is a graph showing moisture-sensitivity characteristics of a conventional moisture-sensitive element.

FIG. 4 shows a change in moisture-sensitivity characteristics at 10% RH to 90% RH obtained after the moisture-sensitive element manufactured in this embodiment was left in a high-temperature, high-humidity atmosphere at about 40° C. and 90% RH. As is apparent from FIG. 4, a moisture-sensitivity characteristic drift at 90% RH of the moisture-sensitive film 3 consisting of the copolymer according to this embodiment is saturated after 200 hours. A drift from an initial value upon saturation corresponds to +7% RH. FIG. 5 shows results obtained after a conventional moisture-sensitive element consisting of celluloseacetatebutyrate as a moisture-sensitive material was left at about 40° C. and 90% RH. As shown in FIG. 5, a drift amount is almost saturated after 100 hours, still showing continuous drift. In this element, a drift from an initial value upon saturation corresponds to +13% RH. Therefore, the moisture-sensitive film 3 according to this embodiment has a drift amount about half that of the conventional moisture-sensitive film and is stable and good. In addition, the hysteresis of the moisture-sensitive film 3 of this embodiment is ½ to ¼ that of the conventional moisture-sensitive film, resulting in good reproducibility. Also, even after the moisture-sensitive film is left in a high-temperature, high-humidity atmosphere or in a single atmosphere for a long time period, its capacitance ratio almost does not change but is stable. Furthermore, when the moisture-sensitive film is left in a high-temperature, high-humidity atmosphere and then returned to a room atmosphere, it reversibly recovers its initial output.

Still another embodiment of the moisture-sensitive element according to the present invention will be described below with reference to FIGS. 1 and 2.

A methyl methacrylate monomer (MMA) purified in reduced-pressure distillation and divinylbenzene (about 30 wt % or less with respect to MMA) are added, and the mixture is stirred and prepolymerized in the presence of a catalyst, thereby preparing a solution having viscosity suitable for a spin coating method. A moisture-sensitive film 3 is formed following the same procedures as in the above embodiments to complete the moisture-sensitive element.

With such an arrangement, the same effects as those of the above embodiments can be obtained.

Note that in the above embodiment, the solution is coated on the lower electrode 2 and then a heat treatment is performed for crosslinking. In place of the heat treatment, however, UV radiation may be radiated to cause copolymerization.

In the above embodiment, the moisture-sensitive element having a sandwich structure has been described. The present invention, however, is not limited to the above embodiments. For example, similar effects can be obtained by applying the present invention to an interdigital moisture-sensitive element in which a pair of interdigital thin-film electrodes are formed to oppose each other on an insulating substrate and a moisture-sensitive film is stacked to cover these thin-film electrodes.

In addition, in the above embodiments, humidity detection is performed on the basis of an electrical capacitance change with respect to a relative humidity of the moisture-sensitive film. The humidity detection, however, may be performed on the basis of an impedance change with respect to the relative humidity.

The moisture-sensitive film in the above embodiments can also be suitably used as a moisture-sensitive film of a moisture sensor in which the moisture-sensitive film is formed on a quartz vibrator and which detects humidity on the basis of a resonance frequency offset caused by water adsorption of the moisture-sensitive film. In addition, the moisture-sensitive film can be suitably used as a moisture-sensitive film of a moisture sensor in which the moisture-sensitive film is formed on a surface elastic wave element and which detects humidity on the basis of a change in speed of a wave passing through the surface elastic wave element.

As described above, according to the moisture-sensitive element of the present invention, the moisture-sensitive film is formed using a polymer prepared by polymerizing a methacrylate monomer not having a hydroxyl group. Therefore, a water adsorption amount is decreased to realize stable moisture-sensitive characteristics with a small drift, a small hysteresis, and a good response, still assuring the enough sensitivity for circuitry implementation. In addition, the moisture-sensitive film is formed using a polymer prepared by copolymerizing methacrylate not having a hydroxyl group and a crosslinking agent having a plurality of vinyl groups. Therefore, a water adsorption amount is controlled to realize a moisture-sensitive element having a small hysteresis, a good response, and high heat, solvent, and environmental resistances and capable of supplying stable outputs.

FIGS. 6A to 6C show an arrangement of a moisture-sensitive element according to the present invention, in which FIG. 6A is a plan view showing its main part, FIG. 6B is a sectional view taken along a line A—A' in FIG. 6A, and FIG. 6C is a sectional view taken along a line B—B' in FIG. 6A. Referring to FIGS. 6A to 6C, reference numeral 11 denotes an insulating substrate consisting of alumina, glass, or a thermal oxide silicon plate; 12, a lower electrode formed on the insulating substrate 11 and consisting of, e.g., a thin Au film; 12a, an electrode terminal of the lower electrode 12; 14, a moisture-sensitive film, as described in the above embodiments, formed on the lower electrode 12 and consisting of, e.g., a polymer material; 15, an upper electrode formed on the moisture-sensitive film 14 and consisting of a thin Au film; and 16, a sensor chip.

Figure 7A:
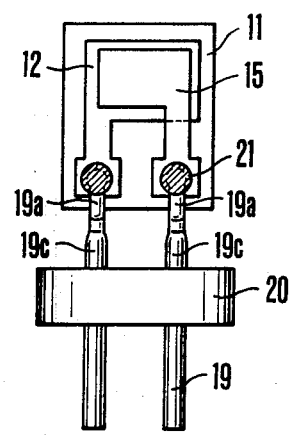
FIGS. 7A and 7B are plan and side views, respectively, of the moisture-sensitive element shown in FIGS. 6A to 6C.
Figure 7B:
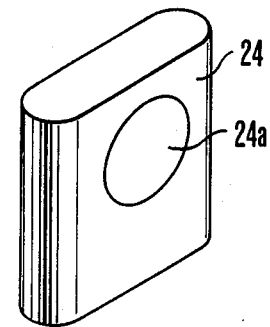
Figure 7B:
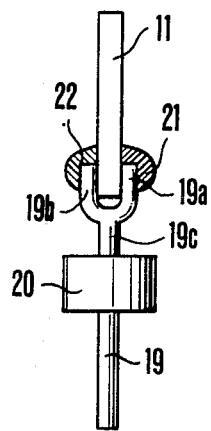

In FIGS. 6A to 6C, each external lead wire 19 has at its distal end portion clip pieces 19a and 19b having a substantially U-shaped opening portion, and its support portion 19c is fixed to an insulating header 20 as shown in FIGS. 7A and 7B. The lead wires 19 are inserted in the lower electrode terminals 12a and an upper electrode terminal 15a, respectively, such that their U-shaped clip pieces 19a and 19b clamp the insulating substrate 11.

Figure 8:
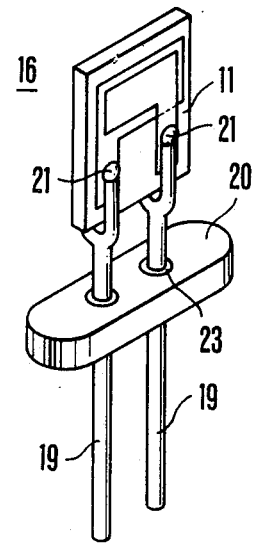
FIG. 8 is a perspective view showing an assembly structure of the moisture-sensitive element shown in FIG. 6.

The dimensional tolerance of the opening portion of the clip pieces 19a and 19b of the lead wire 19 is set so that the insulating substrate 11 can be smoothly inserted and temporarily fixed. Therefore, these lead wires 19 are formed by etching, e.g., thin stainless steel plates. A proper amount of an acryl-, polyester-, phenol-, rubber-, silicone-, or epoxy-based conductive adhesive paste is coated on a contact portion between the upper and lower electrode terminals 12a and 15a on the insulating substrate 11 and the clip piece 19a at one side (front surface side) of each lead wire 19. In addition, a proper amount of, e.g., an epoxy-based adhesive paste is coated on a contact portion between the rear surface of the insulating substrate 11 and the clip piece 19b at the other side (rear surface side) of the lead wire 19 by, e.g., dispenser. The pastes at the front and rear sides are heated at a temperature of 80° to 150° C. for five minutes to five hours to be cured, thereby forming a conductive adhesive portion 21 and a fixing adhesive portion 22, respectively. Thereafter, as shown in FIG. 8, a header 20 in which the lead wires 19 are inserted and fixed by insulating members 23 such as glass or plastic is covered with a cap 24 having an opening portion 24a.

With the above arrangement, the clip pieces 19a of the lead wires 19 are electrically connected to the upper and lower electrode terminals 12a and 15a at the front surface side of the insulating substrate 11. The other clip pieces 19b of the lead wires 19 are mechanically fixed by the fixing adhesive portions 22 at the rear surface side of the insulating substrate 11. Therefore, the sensor chip 16 and the lead wires 19 are mechanically, strongly fixed and electrically connected with each other. In addition, each lead wire 19 is fixed to the header 20. Therefore, since a mechanical stress, vibration, or the like applied to a terminal end portion 19d of the lead wire 19 is absorbed by the header 20 and is hardly transmitted to the connection portions between the sensor chip 16 and the clip pieces 19a and 19b of each lead wire 19. As a result, the connection portions can be reliably protected. Also, the cap 24 protects the surface of the sensor chip 16 from contact and contamination with fingers of an operator upon handling of the sensor chip 16. Therefore, the moisture-sensitive element can stably operate for a long period of time.

As described above, according to the embodiment shown in FIGS. 6A to 8, at least one electrode terminal formed on the insulating substrate and the insulating substrate are clamped by the U-shaped clip pieces formed at the distal end portion of each external lead wire, the contact portion between the electrode terminal and one of the clip pieces is fixed by the conductive adhesive portion, and the contact portion between the rear surface of the insulating substrate and the other contact portion is fixed by the fixing adhesive portion, thereby strongly connecting and fixing the insulating substrate to the external lead wires. Therefore, even when a mechanical stress, vibration, or the like is applied to the insulating substrate or external lead wires, no connection failure occurs at the connection portions, thereby improving both electrical and mechanical reliabilities of the connection portions. In addition, the U-shaped clip pieces are inserted in the insulating substrate, and the front and rear surfaces are fixed by the adhesive portions. Therefore, unlike in a conventional element, no influences of a heat shock nor flux residue occurs upon soldering. As a result, a stable output can be obtained for a long time period, and the number of manufacturing steps is reduced, thereby providing a moisture-sensitive element at low cost.

Figure 9:
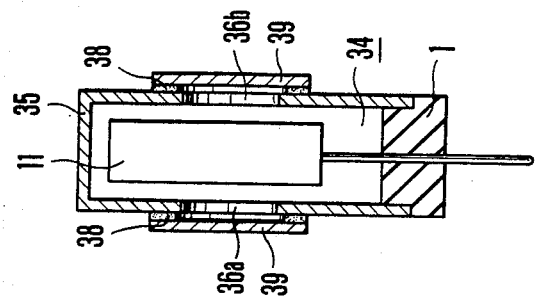
FIG. 9 is a sectional view showing a main part of an embodiment of a humidity detector adopting the moisture-sensitive element.

FIG. 9 is a sectional view showing a main part of a humidity detector to which the moisture-sensitive element of the above embodiment is applied. Referring to FIG. 9, opening portions 36a and 36b are formed in surfaces, opposing a substrate 1 or 11 of the moisture-sensitive element, of a main body case 35 for housing a sensor portion 34 comprising the moisture-sensitive element of the above embodiment. Hydrophobic filters 39 having adhesives 38 coated on their opening peripheral portions are adhered on the opening portions 36a and 36b to cover these portions. Examples of the hydrophobic filter 39 of this type are POLYFURON (tradename : available from TOYO ROSHI K.K.) prepared by molding an ethylene tetrafluoride resin (PTFE) to have a thickness of 0.06 to 0.5 mm, FLUOROPORE (tradename: Sumitomo Electric Industries, Ltd.), ZITEX (tradename: Norton Co.), and TF FILTER (tradename: German Science Japan Co.). Examples of the adhesive 38 are epoxy-, cyanoacrylate-, silicone-, and urethane-based adhesives and an ultraviolet-curing adhesive.

Figure 10:
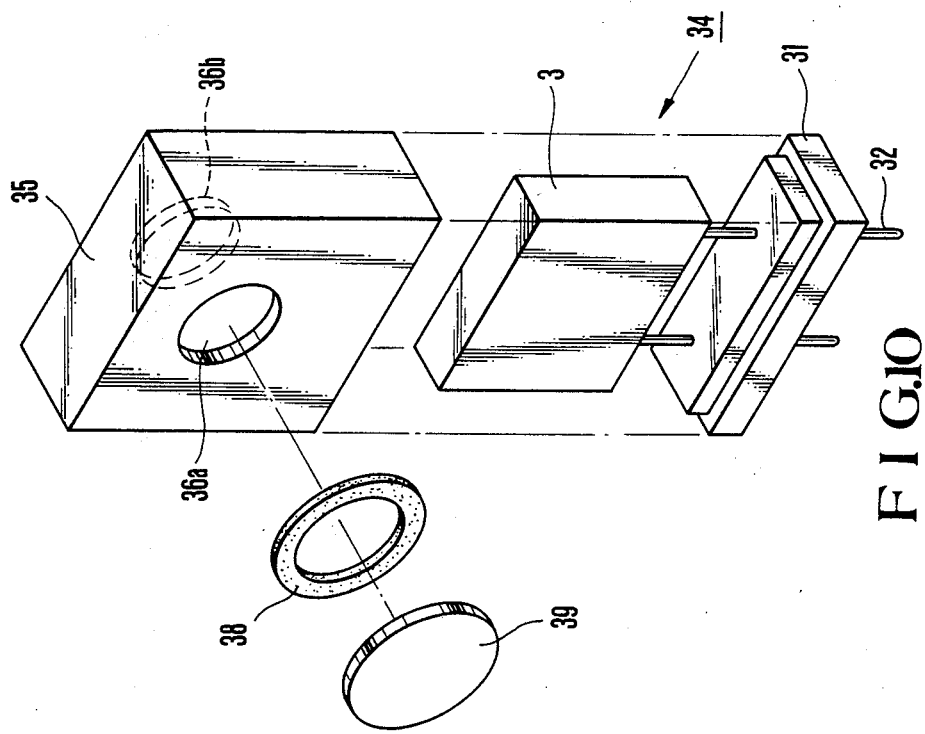
FIGS. 10 and 11 are developed views for explaining a method of manufacturing the humidity detector.
Figure 11:
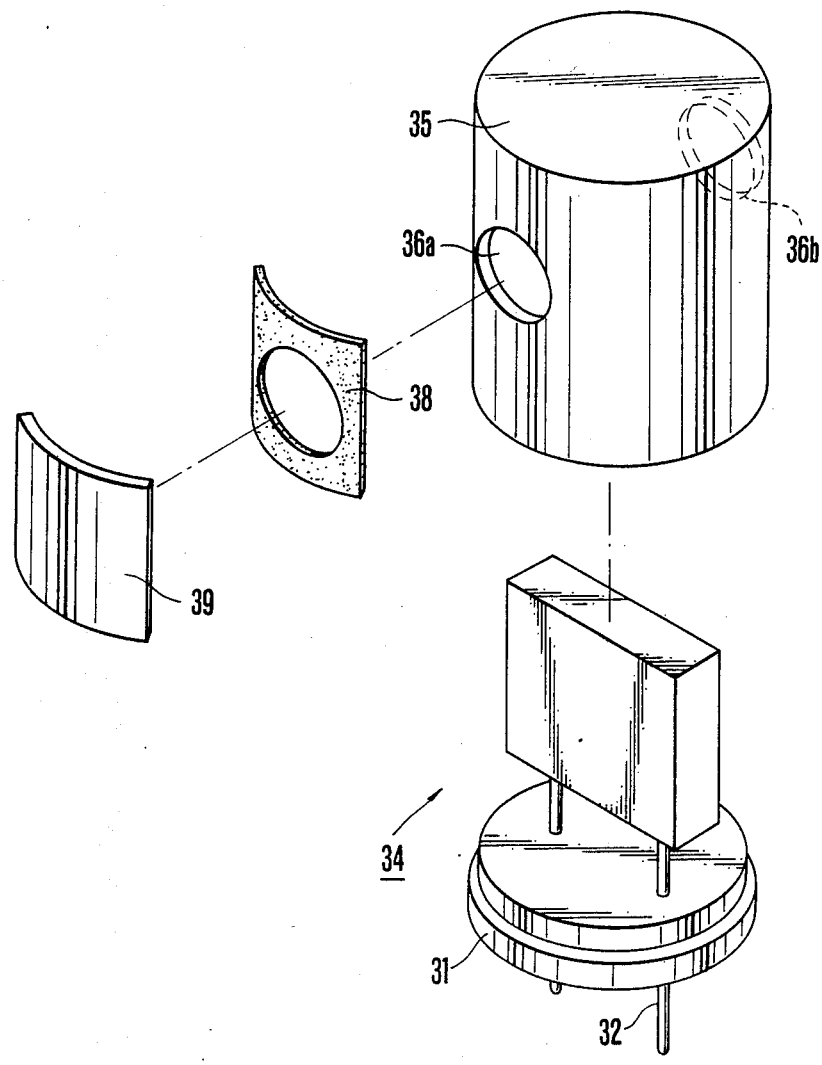

The humidity detector having the above arrangement is manufactured as follows. That is, as shown in FIGS. 10 and 11, a sensor portion 34 as a moisture-sensitive element and lead wires 32 are connected to a base 31, and the base 31 and the main body case 35 having the opening portions 36a and 36b are assembled. The adhesives 38 are coated on an arbitrary area of the peripheral portions on the opening portions 36a and 36b formed in the main body case 35 or the peripheral portions of the hydrophobic filters 39, and the filters 39 are adhered. Thereafter, the adhesives 38 are cured to complete the structure.

With the above arrangement, the hydrophobic filters 39 are adhered on the peripheral portions of the opening portions 36a and 36b of the main body case 35 housing the moisture-sensitive element with a good sealing property. Therefore, only a target detection gas is allowed to reach the moisture-sensitive element in the main body case 35, and water, salt, dust, tobacco smoke and the like do not enter at all, thereby maintaining the prescribed sealing property. In addition, since the hydrophobic filters 39 need only be adhered on the peripheral portions of the opening portions 36a and 36b of the main body case 35, workability can be improved. Furthermore, since the adhesives 38 are coated on the peripheral portions of the hydrophobic filters 39 or the main body case 35, the hydrophobic filters 39 having a thickness of about 0.06 to 0.5 mm can be easily handled.

In the above embodiment, ethylene tetrafluoride (PTFE) filters are used as the hydrophobic filters 39. The present invention, however, is not limited to the above embodiment. For example, the same effects can be obtained by using polyethylene filters or polypropylene filters.

In the above embodiment, the adhesives 38 are used as bonding agents. The present invention, however, is not limited to the above embodiment, but the same effects can be obtained by using tackiness agents.

As described above, according to the embodiment shown in FIGS. 9, 10, and 11, the sealing property between the opening portions of the main body case housing the moisture-sensitive element and the hydrophobic filters is assured. Therefore, superior effects such as improvements in reliability and a service life of the moisture-sensitive element can be obtained.

What is claimed is:

1. A moisture-sensitive element comprising a moisture-sensitive film consisting of a polymer prepared by polymerizing a methacrylate monomer not having a hydroxyl group.

2. An element according to claim 1, wherein said moisture-sensitive film is arranged between first and second electrodes arranged on an insulating substrate.

3. An element according to claim 2, wherein said first electrode is an upper electrode and said second electrode is a lower electrode, said upper and lower electrodes sandwiching said moisture-sensitive film.

4. An element according to claim 2, wherein lead wires are connected to said electrodes.

5. An element according to claim 2, wherein each of said first and second electrodes has an electrode terminal, and further comprising:
 an external lead wire, connected to at least one of said electrode terminals, and having substantially U-shaped clip pieces for clamping said electrode terminal and said insulating substrate;
 a conductive adhesive portion arranged on a contact portion between one of said clip pieces and said electrode terminal to adhere the one clip piece and said electrode terminal; and a fixing adhesive portion arranged at a contact portion between a rear surface of said insulating substrate and the other clip piece to adhere and fix said rear surface and the other clip piece.

6. A moisture-sensitive element comprising a moisture-sensitive film consisting of a polymer prepared by copolymerizing a methacrylate monomer not having a hydroxyl group and a crosslinking agent having a plurality of vinyl groups.

7. A humidity detector, wherein at least one opening portion is formed in a case housing a moisture-sensitive element, and a hydrophobic filter is arranged on said opening portion via a bonding agent, said moisture-sensitive element comprising a moisture-sensitive film consisting of a polymer prepared by polymerizing a methacrylate monomer not having a hydroxyl group.

8. A humidity detector, wherein at least one opening portion is formed in a case housing a moisture-sensitive element, and a hydrophobic filter is arranged on said opening portion via a bonding agent, said moisture-sensitive element comprising a moisture-sensitive film consisting of a polymer prepared by copolymerizing a methacrylate monomer not having a hydroxyl group and a crosslinking agent having a plurality of vinyl groups.

* * * * *